US00PP37599P2

(12) United States Plant Patent
Bagdasarian et al.

(10) Patent No.: US PP37,599 P2
(45) Date of Patent: Aug. 18, 2026

(54) STRAWBERRY PLANT NAMED 'GF Midnight'

(50) Latin Name: ***Fragaria* x *ananassa***
Varietal Denomination: GF Midnight

(71) Applicant: GoodFarms Genetics, LLC, San Diego, CA (US)

(72) Inventors: Jimmy Haig Bagdasarian, Santa Cruz, CA (US); Travis Stegmeir, Salinas, CA (US)

( * ) Notice: Subject to any disclaimer, the term of this patent is extended or adjusted under 35 U.S.C. 154(b) by 0 days.

(21) Appl. No.: 19/370,530

(22) Filed: Oct. 27, 2025

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

(56) References Cited

U.S. PATENT DOCUMENTS

PP34,637 P2 10/2022 Bagdasarian
PP36,984 P2 9/2025 Bagdasarian

*Primary Examiner* — Susan Mccormick Ewoldt
(74) *Attorney, Agent, or Firm* — Phase M Legal

(57) ABSTRACT

A new and distinct variety of strawberry plant named 'GF Midnight' is described here. This new day-neutral strawberry variety is characterized by moderate vigor plants producing attractive, exceptionally firm fruit with a glossy dark red exterior color and complex flavor. The variety performs exceptionally well in cool coastal environments, producing high quality fruit with stable volume throughout the season. This variety also has a compact architecture with low density canopy, which allows ease of picking and spraying.

7 Drawing Sheets

Latin name of the genus and species of the plant claimed: Botanical classification: *Fragaria* x *ananassa.*

Variety denomination: The new strawberry denomination is 'GF Midnight'.

BACKGROUND OF THE INVENTION

The present invention relates to a new and distinct variety of strawberry named 'GF Midnight'. This new day neutral strawberry variety is the result of a controlled cross in an ongoing breeding program made in 2016. The controlled cross, which resulted in the 'GF Midnight' variety was between a strawberry variety designated '101P26', (unpatented), and a strawberry variety designated '012K65', (unpatented).

The controlled cross was carried out in Redding, California, USA. Pollen taken from the field or greenhouse of a '012K65' plant pollinated a female '101P26' plant in a greenhouse. The flowers were emasculated to remove all other pollen sources, and so that no other pollen could contaminate the procedure.

Strawberries developed, were harvested and the seeds resulting from this cross were extracted and germinated in a greenhouse in Redding, California, USA. The resulting seedlings were transplanted to Shastina, California in 2017, grown for an additional period and allowed to propagate asexually via stolons. Plants were then harvested and planted in breeding test plots in early to mid-October in: Oxnard, California (Ventura County); and slightly later in Moss Landing, California (Monterey County). The selection of the new variety was first made in Moss Landing, California, and designated '088W02' in 2017. This selection was later named 'GF Midnight'. The new variety was further propagated asexually by stolons in breeding plots in: Macdoel, California (Siskiyou County); and Manteca, California (San Joaquin County).

The new variety has also been "meristemed." Small pieces of plant material (approximately 0.5 mm in diameter), consisting of the undifferentiated meristem tissue and one or two leaf primordia, were removed from the buds on crowns of young daughter plants, then placed on nutrient medium, and new plants were grown from them. Planting stock from the "meristemed" plants are growing in a screenhouse located in Redding, California.

The propagules of 'GF Midnight' are identical to the original plant in all distinguishing characteristics: accordingly, the propagation has demonstrated that the traits disclosed herein remain fixed and true to type through successive generations of asexual reproduction.

COMPARISON TO PARENT VARIETIES

'GF Midnight' produces very high quality, large, exceptionally firm berries, which are attractive with their glossy dark red appearance, and which have a complex, sophisticated flavor. The primary market for the 'GF Midnight' variety is for fresh market. The berries produced by the 'GF Midnight' variety maintain stable production throughout the season, enabling growers to capitalize on consistent market opportunities. The compact plant architecture with low density canopy allows for more airflow, better spray coverage, and more visible fruit for ease of picking.

The female parent, '101P26', is a day neutral (DN) variety characterized as a moderately vigorous plant which produces medium to large, elongated fruit with good flavor. The male pollen parent, '012K65', is also a day neutral plant, characterized by large, semi-firm, rounded/conical fruit which has a very dark red exterior and interior color but with little glossiness, and a complex and exceptional flavor. Plants of '012K65' are of moderate vigor, with moderately dense foliage.

SUMMARY OF THE INVENTION

'GF Midnight' is a day-neutral variety exhibiting the following combination of characteristics, which have been observed repeatedly, and which distinguish this strawberry plant as a new and distinct variety:

1. The variety produces medium to large sized, exceptionally firm fruit;
2. The fruit exhibits an attractive, glossy dark red exterior;
3. The fruit demonstrates a complex flavor profile with balanced sweetness;
4. The variety produces a high volume of marketable fruit with stable production throughout the season;
5. The flowers extend upright above the canopy, facilitating pollination and harvest visibility; and,
6. The variety performs exceptionally well in cool, coastal environments.

'GF Midnight' fruit demonstrates characteristics and qualities that are highly desired by fresh market strawberry operations. The exceptional firmness provides superior shelf life and shipping durability, critical factors for commercial fresh market success. The complex flavor profile delivers a more sophisticated taste experience than typical commercial varieties. The glossy dark red appearance provides visual appeal while the firm texture maintains quality during transport and storage. Its open-canopy plant architecture with upright flowering facilitates harvesting operations, while the lower leaf density allows for efficient spray coverage and rapid drying after precipitation events. The stable, high-volume production throughout the season, combined with strong disease tolerance, makes 'GF Midnight' particularly well-suited for commercial cultivation in cool, coastal growing regions.

BRIEF DESCRIPTION OF THE FIGURES

The accompanying color photographs, identified as FIGS. 1 through 7, show the appearance of typical specimens of the new strawberry variety, initially designated '088W02', and now named 'GF Midnight'. These Figures depict the colors, as true as it is reasonably possible given differences in color illustrations of this character. Accordingly, color in the photographs may differ slightly from the colors discussed in the botanical description. The photographs of the depicted plant, plant parts, and fruit of 'GF Midnight' were taken in June 2025.

DETAILED BOTANICAL DESCRIPTION OF THE PLANT

Figure 1:
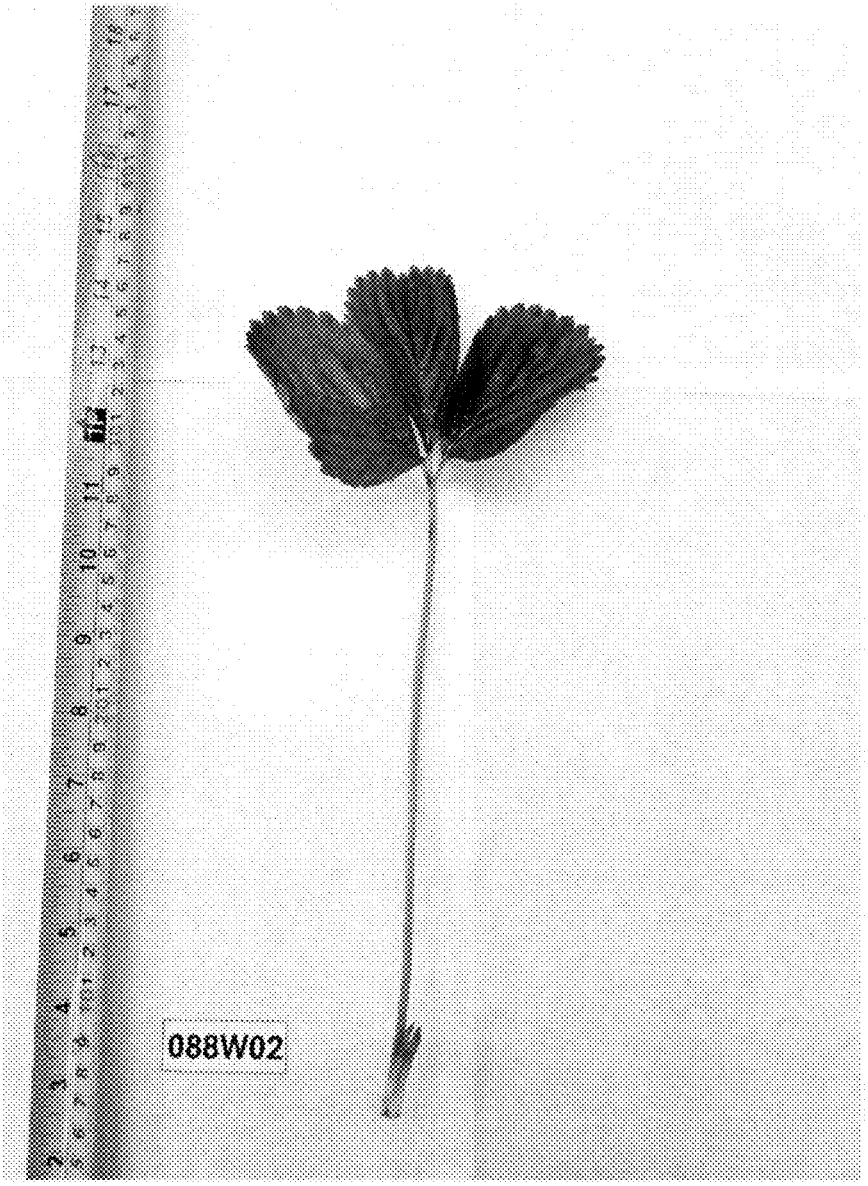
FIG. 1 shows typical leaf and petiole structure at mid-season.
Figure 2:
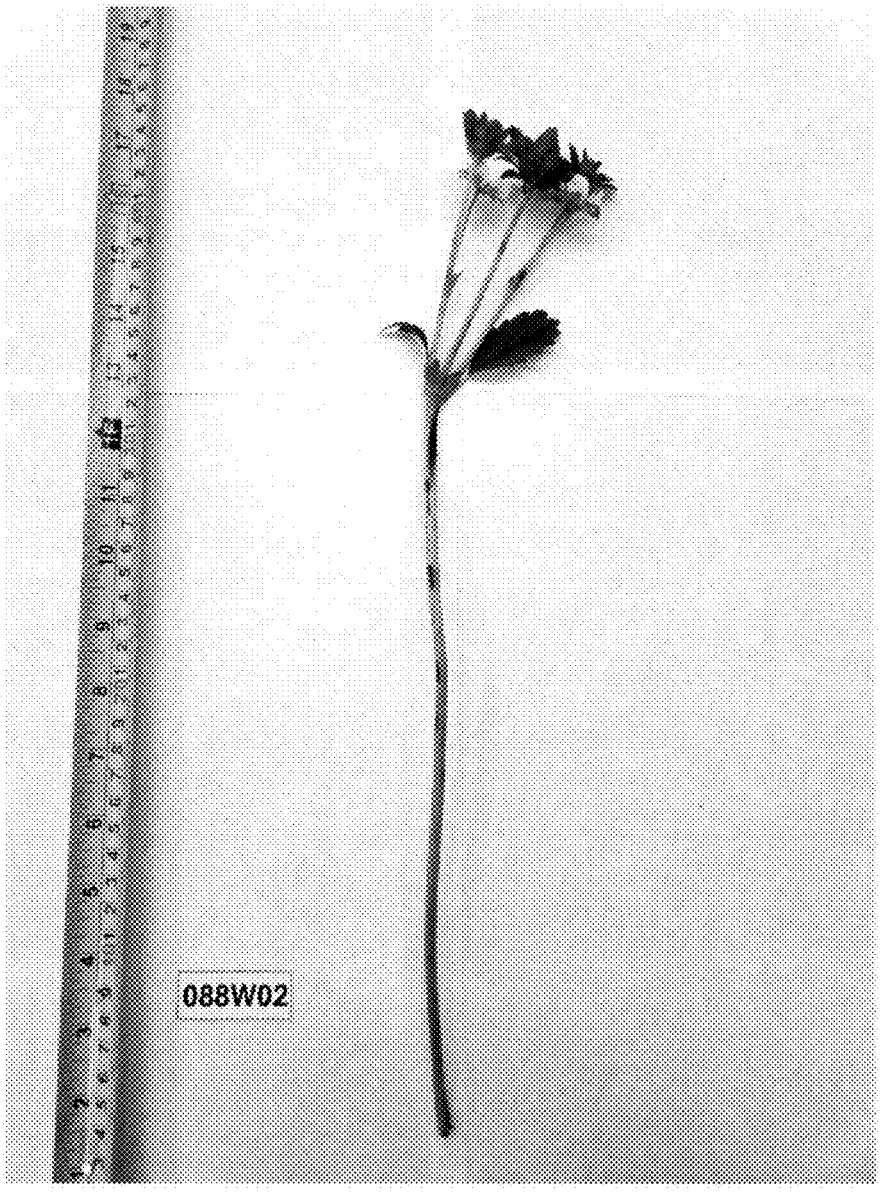
FIG. 2 shows an inflorescence at mid-season.
Figure 3:
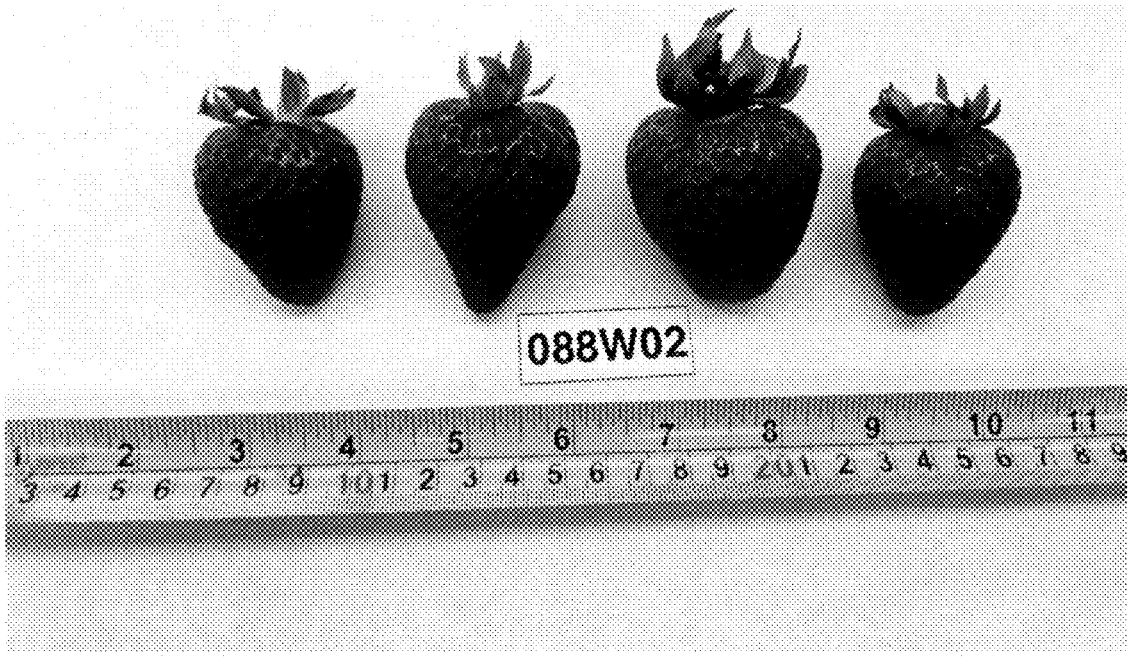
FIG. 3 shows a selection of typical mid-season fruit.
Figure 4:
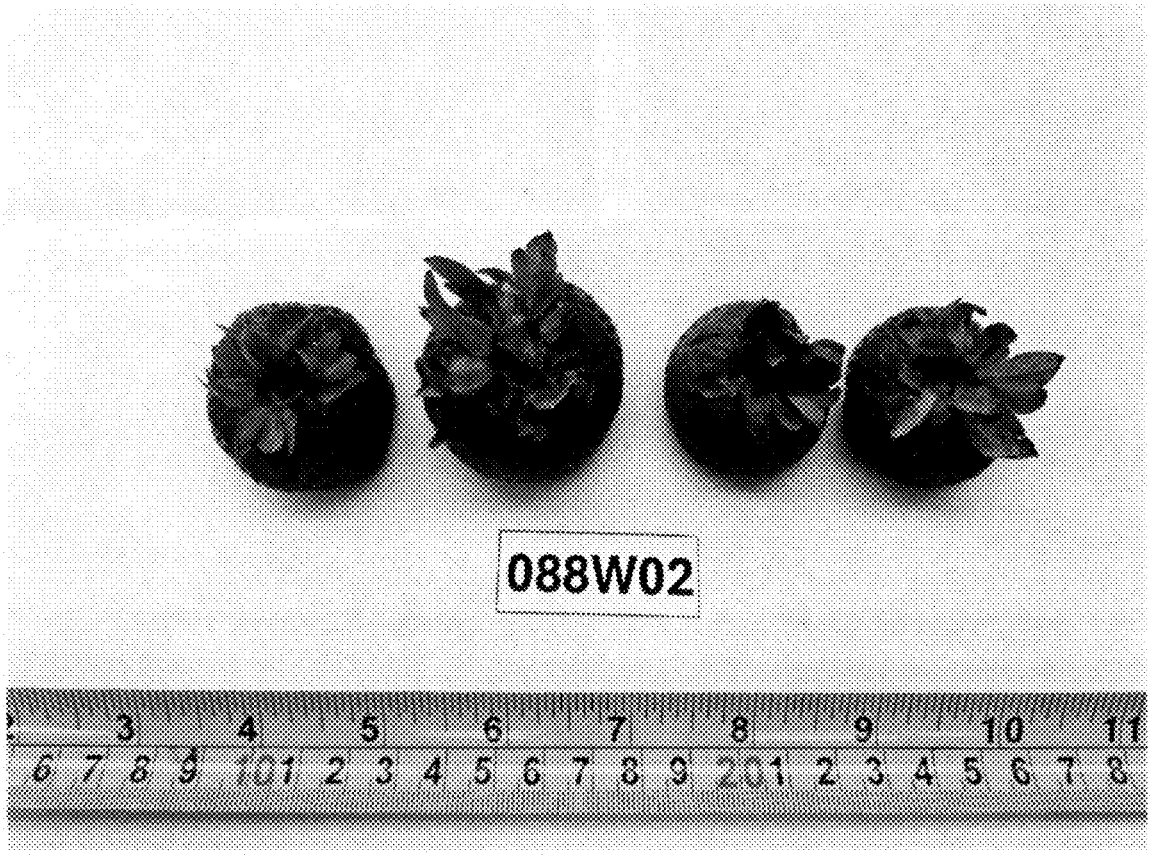
FIG. 4 shows typical calyx position over the berry of 'GF Midnight'.
Figure 5:
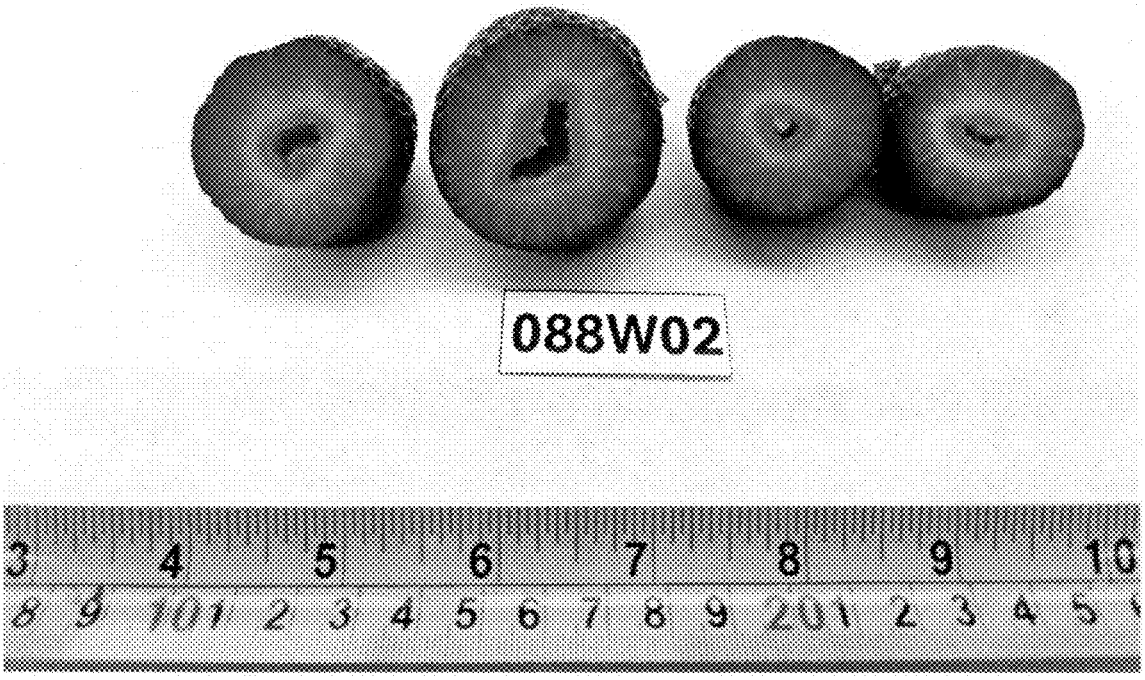
FIG. 5 shows a cross-section of typical fruit internal coloration and core size.
Figure 6:
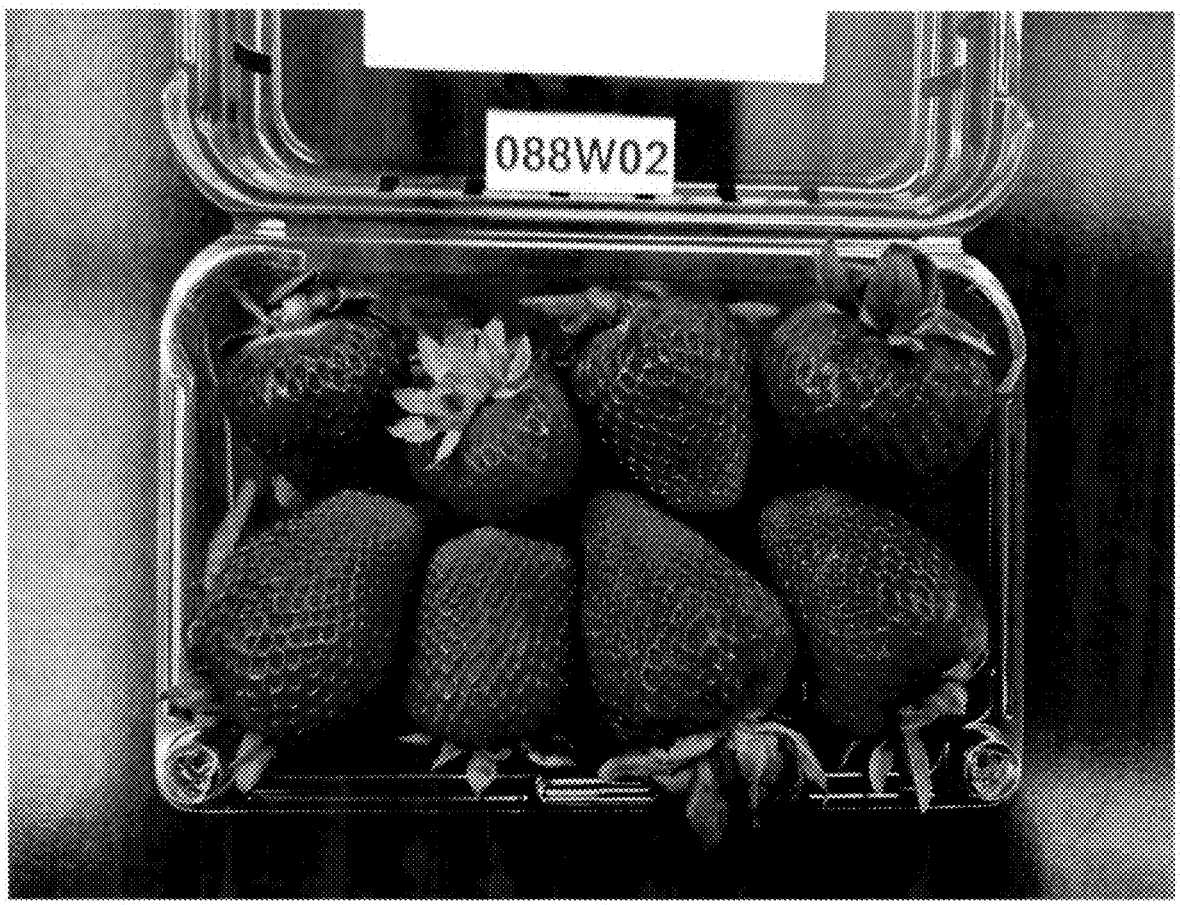
FIG. 6 shows a container of freshly picked fruit.
Figure 7:
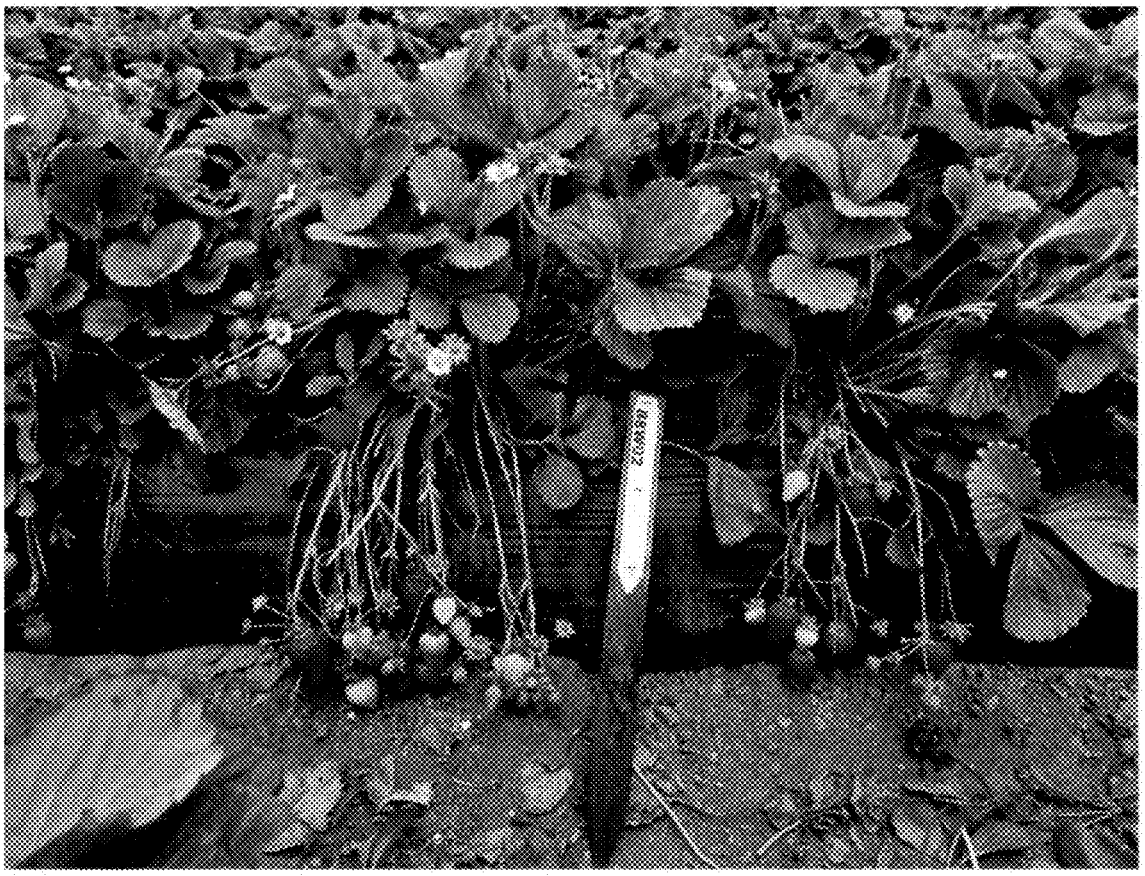
FIG. 7 shows typical plants in a field and the position of flowers in the canopy.

'GF Midnight' is a new and distinct variety of strawberry, known scientifically as *Fragaria* x *ananassa*. It is the result of a cross between its female parent, '101P26', and its male parent '012K65'. Both '101P26' and 012K65 are day neutral, as is 'GF Midnight' Plants of 'GF Midnight' bloom consistently in our high elevation nursery and maintain flowering even in the heat of our low elevation nursery location in Manteca, CA, demonstrating strong day neutral characteristics. The plants of the new variety have moderate vigor and maintain an open architecture during the growing season. 'GF Midnight' exhibits several characteristics which are improvements over one or both of its parent varieties, and other known cultivars. The characteristics of 'GF Midnight' were observed in plants aged about 8 months from planting in the fruiting field. These characteristics and comparisons with other cultivars are discussed following.

The fruit size of 'GF Midnight' falls in between that of its parents, slightly larger than that of '101P26', and slightly larger than that of '012K65'. The size of fruit of 'GF Midnight' is larger during the beginning of the season and slightly decreases at the end but maintains an ideal size range for the fresh market. The fruit of 'GF Midnight' also extends away from the plant on longer pedicels to allow for highly visible fruit and ease of picking, whereas fruit of '012K65' tends to be more hidden under its denser canopy.

'GF Midnight' produces mostly conical fruit, similar to that of the slightly more rounded/conical '012K65', and contrasts the elongated fruit of '101P26'. The fruit of 'GF Midnight' generally ripens evenly from the tip to the shoulders of the berry, resulting in a uniform dark red color over the whole fruit, but has a propensity of developing a seedy tip or a green tip in certain conditions. In contrast, the fruit of '101P26' often has a shoulder that does not ripen all the way to the calyx, and fruit of '012K65' rarely has any seedy tips or shoulder issues. The fruit of 'GF Midnight' is mostly absent of creases and is generally smooth and has a firmness that is firmer than its two parents.

The data set forth for 'GF Midnight' in Tables 1, 2, and 3 was collected in June 2025 from plants grown at a test plot in Moss Landing, Monterey County, California. Color terminology where noted herein was measured using a hand-held Konica Minolta CR-400 colorimeter.

In Table 1, the observed characteristics of 'GF Midnight' are set forth.

TABLE 1

Detailed Description of Characteristics of 'GF Midnight'

| | | |
|---|---|---|
| SPECIFICATION: | | |
| | Genus/Species | *Fragaria X ananassa* |
| | Market Name | Strawberry |
| PARENTS: | | |
| | Female | '101P26' (Unpatented) |
| | Male | '012K65' (Unpatented) |
| PLANT: | | |
| | Type | Day Neutral |
| | Growth Habit | Upright |
| | Foliage density | Low |
| | Vigor | Moderate |
| | Height | Average 36.4 cm; range 31.5 cm to 40.9 cm |

TABLE 1-continued

| Detailed Description of Characteristics of 'GF Midnight' | | |
|---|---|---|
| | Width | Average 39.5 cm; range 37.2 cm to 41.8 cm |
| | Crowns | Multiple crowns produced throughout season |
| | Disease tolerance | Good tolerance to Fusarium<br>Moderate tolerance to Macrophomina<br>Good tolerance to Powdery mildew<br>Moderate tolerance to Verticillium wilt |
| LEAF: | | |
| | Width | Average 13.9 cm; range 13.4 cm to 14.4 cm |
| | Color | Adaxial surface: L*, a*, b *: 36.77, −15.78, 21.60<br>Abaxial surface: L*, a*, b *: 46.97, −14.51 21.74 |
| | Pubescence | Low density |
| | Inter-vein blistering | Slight |
| | Glossiness | Slight |
| | Variegation | None |
| TERMINAL LEAFLET: | | |
| | Length | Average 84.0 mm; range 77.0 mm to 86.0 mm |
| | Width | Average 68.0 mm; range 65.0 mm to 74.0 mm |
| | Ratio Length to width | 1.23 |
| | Margins | Entire to crenate |
| | Leaf shape | Obovate |
| | Base shape | Cuneate |
| | Cross-section shape | Concave to convex |
| PETIOLE: | | |
| | Pubescence | Slight |
| | Petiole color | L*, a*, b *: 48.98, −11.69, 28.44 |
| | Petiole length | Average 24.9 cm; range 20.4 cm to 27.5 cm |
| | Petiole diameter | Average 2.95 mm; range 2.66 mm to 3.08 mm |
| STIPULE: | | |
| | Anthocyanin coloration | Slight |
| | Length | Average 14.5 mm; range 14.27 mm to 17.51 mm |
| | Width | Average 7.59 mm; range 7.4 mm to 8.4 mm |
| STOLON: | | |
| | Anthocyanin coloration | Present, slight |
| | Pubescence | Slight, fine |
| | Diameter | Average 3.64 mm; range 2.8 mm to 3.76 mm |
| INFLORESCENCE: | | |
| | Flowering time | Early |
| | Position | Above canopy |
| | Number of blooms | Average 5.0; range 4 to 5 |
| | Length | Average 38.6 cm; range 34.7 cm to 40.2 cm |
| | Flower diameter | Average 27.0 mm; range 26.0 mm to 29.0 mm |
| | Petal arrangement | Overlapping to separate |
| | Petal number | Average 6.0; range 5 to 7 |
| | Petal length | Average 11.92 mm; range 9.49 mm to 12.42 mm |
| | Petal width | Average 11.78 mm; range 10.85 mm to 12.01 mm |
| | Ratio Length to width | 1.01 |

TABLE 1-continued

| Detailed Description of Characteristics of 'GF Midnight' | | |
|---|---|---|
| | Petal color | L*, a*, b *: 74.74, -1.79, 4.57 |
| | Calyx | Larger than the corolla |
| | Calyx color (adaxial) | L*, a*, b *: 39.76, −15.49, 25.31 |
| | Calyx color (abaxial) | L*, a*, b *: 47.19, −14.20, 23.51 |
| | Stamens | Average 30.0; range 30 to 36 |
| | Pedicel | Attitude of hairs mostly perpendicular |
| FRUIT: | | |
| | Bearing | Day neutral |
| | Shape | Conic |
| | Weight | Seasonal average: 27.0 g |
| | Achenes | Acutely below fruit surface |
| | Glossiness | High |
| | External color | L*, a*, b *: 23.21, 26.86, 10.04 |
| | Internal color | L*, a*, b *: 56.02, 27.87, 28.05 |
| | Evenness of external color | Mostly even |
| | Width of band at top devoid of achenes | Slight |
| | Yield | Approximate grams per plant: 1,230 g |
| | Firmness | Very firm |
| | % Brix | Average: 8.3; range 6.4 to 10.27 |

Plants and Foliage

The comparison statistics set forth in the following tables are with respect to characteristics observed at mid-season. All measurements for 'GF Midnight' were taken at a test plot in Moss Landing, Monterey County, California during 2025. In Tables 2 and 3, the characteristics of 'GF Midnight' are compared with historical data of patented varieties 'Ashley Jay' (U.S. Plant Pat. No. 34,637) and 'GF Belle' (U.S. Plant Pat. No. 36,984).

The form and structure of the plants of 'GF Midnight' are similar in height to that of 'Ashley Jay' and slightly larger than 'GF Belle'. The plant spread of 'GF Midnight' is smaller than that of either 'GF Belle' or 'Ashley Jay'. The canopy of 'GF Midnight' is much more open than that of 'Ashley Jay' and similar to that of 'GF Belle'. The leaf surface of 'GF Midnight' shows a slight blistering, on par with that of 'Ashley Jay' and 'GF Belle'. The glossiness of the leaves of 'GF Midnight' is less glossy than that of 'Ashley Jay' and 'GF Belle'. The petioles of 'GF Midnight' are notably thinner than both comparison varieties.

In Table 2, comparative data for foliar characteristics are presented for 'GF Midnight' and historical data of two comparison cultivars, 'Ashley Jay' and 'GF Belle'.

TABLE 2

Foliar Characteristics of 'GF Midnight' Compared-'Ashley Jay' and 'GF Belle'

| Foliar Characteristics | | Cultivar | |
|---|---|---|---|
| | | 'GF Belle' | 'Ashley Jay' |
| Plant height (mm) | Average | 323 | 369 |
| | Range | 284-358 | 330-410 |
| Plant spread (mm) | Average | 426 | 515 |
| | Range | 418-461 | 460-570 |
| Leaf width (mm) | Average | 142 | 152 |
| | Range | 127-153 | 135-167 |

TABLE 2-continued

Foliar Characteristics of 'GF Midnight' Compared-'Ashley Jay' and 'GF Belle'

| | | | |
|---|---|---|---|
| Mid-tier leaflet length (mm) | Average | 100.5 | 96 |
| | Range | 81.9-115.1 | 81-115 |
| Mid-tier leaflet width (mm) | Average | 88.2 | 88 |
| | Range | 77.3-108.1 | 69-104 |
| Petiole length (mm) | Average | 290 | 281 |
| | Range | 282-301 | 250-308 |
| Petiole diameter (mm) | Average | 4.33 | 4.59 |
| | Range | 3.87-4.81 | 3.72-5.81 |
| Number leaflets per leaf | | 3 | 3 |
| Leaf convexity | | Concave | Slight concave |
| Shape leaflet base | | Obtuse | Cuneate |
| Leaf pubescence | | Low density | Medium density |
| Petiole pubescence | | Low density | Slight |
| Stipule length (mm) | Average | 13.3 | 15.42 |
| | Range | 11.8-15.1 | 9.7-19.3 |
| Stipule anthocyanin coloration | | Slight | Slight |
| Leaf margins | | Crenate | Crenate |
| Leaf color adaxial surface (L*, a*, b*) | | 36.69, −13.89, 20.07 | 36.69, −13.89, 20.07 |
| Leaf color abaxial surface (L*, a*, b*) | | 53.87, −13.74, 22.74 | 53.87, −13.74, 22.74 |
| Petiole color (L*, a*, b*) | | 54.10, −10.69, 23.19 | 53.10, −13.59, 31.10 |
| Leaf surface blistering | | Slight | Slight |
| Leaf surface glossiness | | Moderate | Moderate |

| Foliar Characteristics | | Cultivar GF Midnight' |
|---|---|---|
| Plant height (mm) | Average | 364 |
| | Range | 315-409 |
| Plant spread (mm) | Average | 395 |
| | Range | 372-418 |
| Leaf width (mm) | Average | 139 |
| | Range | 134-144 |
| Mid-tier leaflet length (mm) | Average | 84 |
| | Range | 77-86 |
| Mid-tier leaflet width (mm) | Average | 68 |
| | Range | 65.0-74.0 |
| Petiole length (mm) | Average | 249 |
| | Range | 204-275 |
| Petiole diameter (mm) | Average | 2.95 |
| | Range | 2.66-3.08 |
| Number leaflets per leaf | | 3 |
| Leaf convexity | | Concave to convex |
| Shape leaflet base | | Cuneate |
| Leaf pubescence | | Low density |
| Petiole pubescence | | Slight |
| Stipule length (mm) | Average | 14.5 |
| | Range | 14.27-17.51 |
| Stipule anthocyanin coloration | | Present, slight |
| Leaf margins | | Entire to crenate |
| Leaf color adaxial surface (L*, a*, b*) | | 32.67, −13.02, 18.02 |
| Leaf color abaxial surface (L*, a*, b*) | | 49.88, −13.00, 22.74 |

TABLE 2-continued

Foliar Characteristics of 'GF Midnight' Compared-'Ashley Jay' and 'GF Belle'

| | |
|---|---|
| Petiole color (L*, a*, b*) | 48.98, −11.69, 28.44 |
| Leaf surface blistering | Slight |
| Leaf surface glossiness | Slight |

Flowering and Fruit

'GF Midnight' is a day-neutral variety that produces flowers continuously throughout the growing season under cool, coastal climate conditions. 'GF Midnight' has longer pedicel length than the other two varieties, which means the flowers and fruit are held further away from the plant canopy, facilitating better air circulation and easier harvesting access. When compared to their individual plant size, all three varieties produce flowers that are near or above the canopy level, leaving flowers exposed to pollinators, with 'GF Midnight' having most flowers exposed. The dark red exterior color of the fruit of 'GF Midnight' is distinctly darker than both 'Ashley Jay' and 'GF Belle'. The fruit of 'GF Midnight' has excellent culinary qualities, including good firmness, size, attractive dark red glossy color, and a complex flavor profile.

In Table 3, comparative data for flower and fruit characteristics for 'Ashley Jay', 'GF Belle', and 'GF Midnight', are set forth.

TABLE 3

Flower and Fruit Characteristics of 'GF Midnight' Compared to 'Ashley Jay' and 'GF Belle'

| Characteristic | | Cultivar 'GF Belle' | 'Ashley Jay' | 'GF Midnight' |
|---|---|---|---|---|
| Petal number | | 5-8 | 5-8 | 5-7 |
| Petal length (mm) | Average | 12.8 | 12.39 | 11.92 |
| | Range | 9.83-14.9 | 9.74-15.28 | 9.49-12.42 |
| Petal width (mm) | Average | 11.9 | 12.27 | 11.78 |
| | Range | 9.1-13.9 | 9.24-14.93 | 10.85-12.01 |
| Position of flower (relative to foliage) | | Most exposed | Most even | Most exposed |
| Pedicel length (mm) | Average | 372 | 336 | 386 |
| | Range | 342-431 | 270-422 | 347-402 |
| Sepal color (adaxial) | (L*, a*, b*) | 34.88, −12.31, 15.90 | 31.55, −10.36, 13.26 | 39.76, −15.49, 25.31 |
| Sepal color (abaxial) | (L*, a*, b*) | 50.50, −13.45, 10.31 | 43.01, −14.20, 21.77 | 47.19, −14.20, 23.51 |
| Flower diameter (mm) | Average | 28.18 | 25.8 | 27.0 |
| | Range | 23.5-34.2 | 22.4-29.1 | 26.0-29.0 |
| Fruit color (external) | (L*, a*, b*) | 33.86, 33.08, 19.62 | 40.99, 41.96, 29.56 | 23.21, 26.86, 10.04 |
| Fruit color (internal) | (L*, a*, b*) | 49.39, 35.64, 35.72 | 54.75, 34.16, 37.50 | 56.02, 27.87, 28.05 |

We claim:

1. A new and distinct strawberry plant named 'GF Midnight' as described and illustrated herein.

* * * * *